United States Patent [19]
Takanishi et al.

[11] Patent Number: 5,565,440
[45] Date of Patent: Oct. 15, 1996

[54] METHANE DIPHOSPHONIC ACID DERIVATIVE, ITS PRODUCTION PROCESS AND ITS PHARMACEUTICAL APPLICATIONS

[75] Inventors: Keijiro Takanishi, Kamakura; Norio Kawabe, Fujisawa; Teruo Nakadate, Yokohama, all of Japan

[73] Assignee: Toray Industries, Inc., Japan

[21] Appl. No.: 256,186

[22] PCT Filed: Oct. 29, 1993

[86] PCT No.: PCT/JP93/01579

§ 371 Date: Jun. 28, 1994

§ 102(e) Date: Jun. 28, 1994

[87] PCT Pub. No.: WO94/10181

PCT Pub. Date: May 11, 1994

[30] Foreign Application Priority Data

Oct. 30, 1992 [JP] Japan ................... 4-292685

[51] Int. Cl.$^6$ ............... A61K 31/38; C07D 333/64; C07D 335/06; C07D 337/08
[52] U.S. Cl. ................ 514/63; 514/96; 549/4; 549/5; 549/8; 558/89
[58] Field of Search ............. 549/4, 5, 8; 514/63, 514/96; 558/89

[56] References Cited

U.S. PATENT DOCUMENTS 5,159,108  10/1992  Kieczykowski ............. 562/13

FOREIGN PATENT DOCUMENTS

| 0440809 | 8/1991 | European Pat. Off. . |
| 0481920 | 4/1992 | European Pat. Off. . |
| 9203451 | 3/1992 | WIPO . |
| 9305052 | 3/1993 | WIPO . |

OTHER PUBLICATIONS

Evans et al., "New Silicon–Phosphorus Reagents . . . " J. Am. Chem. Soc., vol. 100, No. 11, May 24, 1978, pp. 3467–3477.

Pudovik et al., "Reaction of a trimethylsilyl phosphite . . . ", Zh. Obshch. Khim., 43(3), 1973, p. 680 (Abstract Only).

Primary Examiner—José G. Dees
Assistant Examiner—Mary C. Cebulak
Attorney, Agent, or Firm—Austin R. Miller

[57] ABSTRACT

The present invention discloses a methane diphosphonate derivative, a process for producing said derivative and its pharmaceutical applications, said methane diphosphonate derivative indicated with general formula (1):

(wherein, $R_1$, $R_2$, $R_3$ and $R_4$ are independently a pharmacologically acceptable cation, a hydrogen atom or a straight chain or branched alkyl group having 1–4 carbon atoms, $R_5$ is a hydrogen atom or a trialkylsilyl group, m is an integer of 0 to 3, n is an integer of 1 to 3, $R_6$ and $R_7$ are independently a hydrogen atom or an alkyl group, and X represents a hydrogen atom, a halogen atom, an alkyl group, an alkoxy group or an alkylthio group).

The compounds of the present invention are useful as an anti-inflammatory, antipyretic, analgesic, antirheumatic drug, antiarthritic or anti-osteoporosis drug as a result of having anti-inflammatory action, antipyretic and an algesic action, or action which improves bone metabolic disorders caused by rheumatism, arthritis, osteoporosis and so forth.

16 Claims, No Drawings

METHANE DIPHOSPHONIC ACID DERIVATIVE, ITS PRODUCTION PROCESS AND ITS PHARMACEUTICAL APPLICATIONS

SPECIFICATION

This application is a 371 of PCT/JP93/01579 filed Oct. 29, 1993.

1. Technical Field

The present invention relates to novel methane diphosphonic acid derivatives, useful as pharmaceuticals such as an anti-inflammatory drug, antirheumatic drug, bone metabolic disease drug and so forth, and its production process.

2. Background Art

Compounds having a diphosphonate structure are known for use as an anti-inflammatory drug, antiarthritics and so forth according to, for example, Japanese Unexamined Patent Publication (Kokai) No. 59-42395, Japanese Unexamined Patent Publication (Kokai) No. 58-174393 and Japanese Unexamined Patent Publication (Kokai) No. 58-174394. Moreover, Japanese Unexamined Patent Publication (Kokai) No. 60-174792 contains a description to the effect that 1-substituted-amino-1-substituted-thioalkylmethylene diphosphonate is effective as an antirheumatic drug. In addition, clinical studies have been conducted using sodium (1-hydroxyethylidene)bisphosphonate as a drug for treatment of osteoporosis. Although various other compounds having a methane diphosphonate structure have been studied for use in the treatment of inflammatory diseases and calcium metabolism disorders, these compounds are still inadequate in terms of their inhibitory effects on inflammation, thus resulting in a desire for further improvement.

On the other hand, 5-lipoxygenase inhibitor in the arachidonic acid cascade, an inhibitor for Interleukin-1 which is an important inflammatory cytokine, and an inhibitor (antioxidant) for active oxygen released by neutrophils at sites of inflammation, and so forth have recently attracted attention as a new non-steroid anti-inflammatory drug, and research has been conducted actively on these compounds. For example, 2,4-di-isobutyl-6-(N,N-dimethylaminomethyl)phenol, i.e., a compound which demonstrates both antioxidative action and action that inhibits the production of Interleukin-1, is disclosed in Japanese Unexamined Patent Publication (Kokai) No. 63-258410; 4,4-(isopropylidenedithio)bis(2,6-di-tertbutyl)phenol, as an inhibitor for the production of interleukin-1, is disclosed in Japanese Unexamined Patent Publication (Kokai) No. 63-258408; and 3,5-di-tert-butyl-4-hydroxycinnamic amide as an inhibitor for 5-lipoxygenase is disclosed in Japanese Unexamined Patent Publication (Kokai) No. 63-130570. However, in all cases, anti-inflammatory effects are either weak or not observed in vivo, thus making it difficult to say that these substances have practical efficacy.

Conventional synthetic methods employed for the hydroxymethane diphosphonates pertaining to the compounds of the present invention is described in, for example, Japanese Unexamined Patent Publication (Kokai) No. 57-31691 and Japanese Unexamined Patent Publication (Kokai) No. 58-174394.

Although a reaction is indicated in Japanese Unexamined Patent Publication (Kokai) No. 57-31691 wherein the corresponding carboxylic acid is converted directly to a diphosphonic acid without going through the phosphonic acid ester, in consideration of the use of strongly acidic compounds in the form of phosphorous trichloride and phosphorous acid as reaction reagents and a high temperature of 100° C. being required to carry out the reaction, this reaction cannot be applied in cases when the target compound is decomposed or denatured under strongly acidic or high temperature conditions.

Moreover, although dialkyl phosphite is used during conversion of acyl phosphonic acid ester into the corresponding diphosphonic acid ester in the reaction indicated in Japanese Unexamined Patent Publication (Kokai) NO. 58-174394, a catalytic amount of base is essential in this reaction. Thus, in order to obtain the target diphosphonic acid ester in satisfactory yield, it is necessary to isolate and purify the acyl phosphonic acid ester as an intermediate of the reaction. When considering that acyl phosphonic acid ester is easily decomposed to carboxylic acid under acidic conditions, it is difficult to say that the process described in Japanese Unexamined Patent Publication (Kokai) No. 58-174394 is a satisfactory process for disphosphonic acid ester synthesis.

As described above, since the conventional processes have numerous disadvantages such as severe reaction conditions or the need to isolate an unstable intermediate, a technique having a simple synthesis procedure that allows synthesis under gentler reaction conditions than those of the conventional processes is sought for the synthesis of hydroxymethane diphosphonate having a wider range of substituent groups.

The inventors of the present invention conducted research to develop a non-steroid anti-inflammatory drug, focusing on 5-lipoxygenase in the arachidonic acid cascade, Interleukin-1 and an inhibitor for active oxygen, as well as phosphonic acid for use in the treatment of bone metabolic disorders. As a result, it was found that effects not found in existing drugs were generated against inflammations relating to bone metabolic disorders by combining a 1-thiabenzocycloaikane structure with a hydroxymethane diphosphonate structure.

The object of the present invention is to provide a novel hydroxymethane diphosphonate compound that is useful as a pharmaceutical having excellent anti-inflammatory effects and its production process.

DISCLOSURE OF THE INVENTION

The present invention provides the useful novel compounds of the structure indicated below in order to achieve the above-mentioned object. Namely, the present invention relates to a methane diphosphonate derivative represented by the general formula (1):

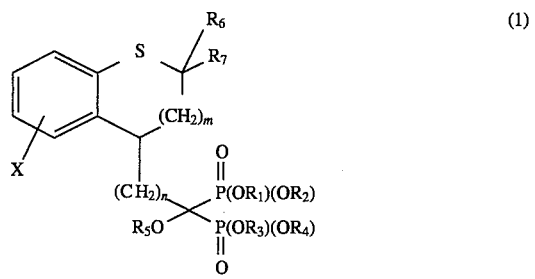

(wherein, $R_1$, $R_2$, $R_3$ and $R_4$ are independently a pharmacologically acceptable cation, a hydrogen atom or a straight chain or branched alkyl group having 1–4 carbon atoms, $R_5$ is a hydrogen atom or a trialkylsilyl group, m is an integer of 0 to 3, n is an integer of 1 to 3, $R_6$ and $R_7$ are independently a hydrogen atom or an alkyl group, and X represents a hydrogen atom, a halogen atom, an alkyl group, an alkoxy group or an alkylthio group), a process for producing said derivative, and its pharmaceutical applications.

DETAILED DESCRIPTION OF THE INVENTION $R_1$, $R_2$, $R_3$ and $R_4$ are each independent, and the pharmacologically allowable cations of $R_1$–$R_4$ are metal cations, ammonium, amine cat ions or quaternary ammonium ion. Particularly preferable examples of metal cations include those derived from alkaline metals such as lithium, sodium and potassium, as well as alkaline earth metals such as magnesium and calcium. The cations of other metals such as aluminum, zinc and iron are also included in the present invention. Cations of sodium, potassium or ammonium are particularly preferable. In addition, the cations in $R_1$, $R_2$, $R_3$ and $R_4$ may be identical or different, and mixtures of cations and hydrogen atoms, examples of which include monocationic salts, bicationic salts and tricationic salts, are also included in the present invention.

Examples of straight chain or branched alkyl groups having 1–4 carbon atoms used as $R_1$, $R_2$, $R_3$ and $R_4$ include methyl, ethyl, propyl, isopropyl, butyl, isobutyl and t-butyl groups.

The cations, hydrogen atoms and alkyl groups used for $R_1$, $R_2$, $R_3$ and $R_4$ may be present together.

The trialkylsilyl group used as R5 has an alkyl group having 1–6 carbon atoms, examples of which include trimethylsilyl, dimethylisopropylsilyl, methyldiisopropylsilyl, triethylsilyl, diethylisopropylsilyl, dimethyl-t-butylsilyl, di-t-butylmethylsilyl, hexyldimethylsilyl and triisopropylsilyl groups.

The alkyl group used as $R_6$ and $R_7$ has 1–4 carbon atoms, examples of which include methyl, ethyl, propyl, isopropyl and butyl groups. The hydrogen atoms and alkyl groups used as $R_6$ and $R_7$ may be the same or different.

Examples of halogens used as the substitution group X include fluorine, chlorine, bromine and iodine. The alkyl group, alkoxy group and alkyl portion of the alkylthio group used as the substitution group X refer to straight chain or branched alkyl groups having 1–8 carbon atoms, examples of which include methyl, ethyl, propyl, isopropyl, butyl, isobutyl, t-butyl, pentyl, hexyl, cyclobutyl, cyclopentyl, cyclohexyl, cyclopentylmethyl and cyclohexylmethyl groups. There is no particular limitation on the location of substitution.

In synthesizing the compounds of the present invention, the carboxylic acid indicated in general formula (2) can be synthesized by known processes. As an example, the process for synthesis of 4-(substituted-thiochromanyl)methane carboxylic acid ($R_6$, $R_7$=H, n=m=1) (2') is shown below.

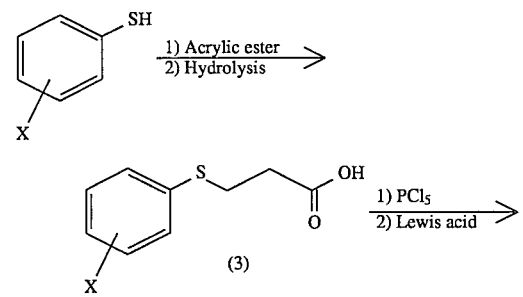

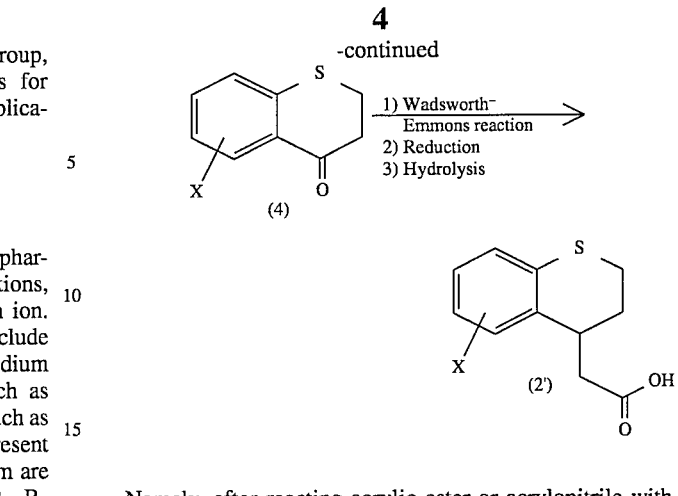

Namely, after reacting acrylic ester or acrylonitrile with an aromatic thiol, either commercially available or able to be synthesized byknownmethods, in the presence of a basic catalyst, alkaline hydrolysis is carried out to convert to carboxylic acid (3) (wherein X is the same as previously defined). Next, after converting to the acid chloride using phosphorous pentachloride and allowing the Lewis acid to act without isolating the acid chloride, the thiochromanone (4) (wherein X is the same as previously defined) is obtained. After then performing the Wadsworth-Emmons reaction or the Knoevenagel reaction on this thiochromanone and reducing the resulting unsaturated ester or unsaturated nitrile with hydrogen or metal magnesium and so forth, hydrolysis is performed to obtain the thiochromanylmethane carboxylic acid represented by the general formula (2') (wherein X is the same as previously defined).

Compound (1) of the present invention can be produced according to the process represented in the following reaction formula using the carboxylic acid represented by the general formula (2) as the starting material. Furthermore, since the reaction temperature and reaction time in this process vary according to the reagents and solvents used, the conditions below merely indicate the preferable conditions.

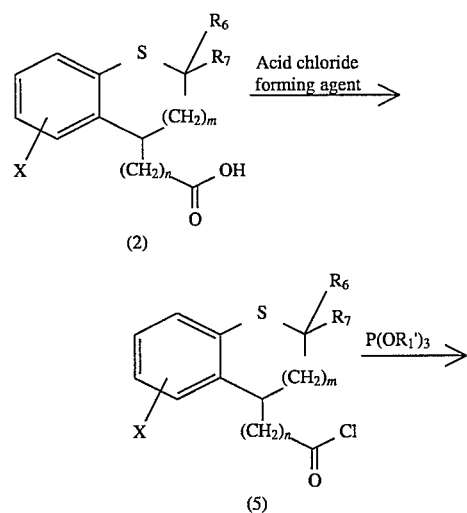

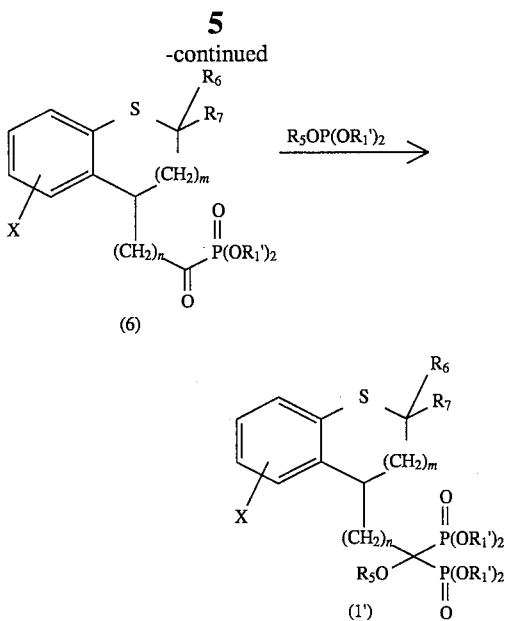

(wherein, $R'_1$ is a straight chain or branched alkyl group having 1–4 carbon atoms, $R_5$ is a trialkylsilyl group, and X, $R_6$, $R_7$, m and n are the same as previously defined).

By reacting carboxylic acid (2) with an acid chloride forming agent such as oxalic chloride or thionylchloride in the presence of a catalytic amount of dimethylformamide in a suitable solvent such as tetrahydrofuran, carboxylic acid (2) is converted to the corresponding acid chloride (5). At this time, 1–3 equivalents with respect to carboxylic acid (2), of the acid chloride forming agent such as oxalic chloride is used, the reaction temperature is −20° to 100° C., and the reaction time is 0.5–5 hours. Next, by reacting trialkylphosphite with acid chloride (5) in a suitable solvent such as tetrahydrofuran, acid chloride (5) is converted to acylphosphonate ester (6) which is a reaction intermediate. 1–3 equivalents with respect to acid chloride (5), of trialkylphosphite are used, the reaction temperature is −20° to 100° C. and the reaction time is 0.5–5 hours. Subsequently, by adding dialkyltrialkylsilyl-phosphite, easily synthesized using the technique of Chevnyshev, E.A. (Zh. Obsh. Khim. 45, 242 (1975)) and so forth, to the reaction solution, acylphosphonate ester (6) can be converted to the diphosphonate ester represented by the general formula (1'). 1–3 equivalents of dialkyltrialkyl silylphosphite are used with respect to acylphosphonate ester (6), the reaction temperature is −20° to 100° C. and the reaction time is 0.5–5 hours.

The alkyl group in the trialkyl of trialkylphosphite and in the dialkyl of dialkyltrialkylsilylphosphite represent straight chain or branched alkyl groups having 1–4 carbon atoms of $R_1$ to $R_4$ in general formula (1), while the trialkylsilyl group is used as $R_5$ of general formula (1).

The synthesis process of the present invention as described above is useful as a process for synthesizing diphosphonic acid ester with respect to involving a simple experimental procedure and being able to obtain the target compound under mild conditions.

The diphosphonic acid in which $R_1$, $R_2$, $R_3$ and $R_4$ of the compound represented by the general formula (1) are hydrogen atoms is obtained by hydrolysis from the diphosphonic acid ester (1') in which $R_1$, $R_2$, $R_3$ and $R_4$ of the compound represented by the general formula (1) are alkyl groups. Although this can be carried out by ordinary known methods, it can also be carried out by, for example, treating the ester with trimethylsilylbromide usually at normal temperature. Following isolation, the acid thus obtained can be converted to one type of its salts using a known method. In the case $R_5$ is a trialkylsilyl group, desilylation can also be carried according to known methods when necessary.

The target diseases of the compounds of the present invention are inflammatory diseases, diseases with pain and bone metabolic disorders.

The object of the present invention is to provide a drug having excellent treatment and preventive properties against, for example, reumatoid arthritis, rheumatoid polyarthritis, osteoarthritis, scapulohumeral periarthritis, neck, shoulder and arm syndrome, discopathy, lumbago, tendinitis and peritendinitis, athrosteitis, subacromial bursitis, fibrositis, muscle pain, neuralgia, gout, and post-surgical or post-trauma inflammation and swelling (when used as an anti-inflammatory, antirheumatic drug, anti-arthritis drug or analgesic), as well as osteoporosis, Paget's disease, Bechterew's disease, hypercalcemia and ectopic ossification (bone metabolic disorders).

In the case of using the novel methane diphosphonate compound of the present invention in the above-mentioned applications, it may be provided as is or as a pharmaceutical composition mixed with a known pharmacologically acceptable carrier, vehicle and so forth. Administration may be performed either by oral administration in the form of a tablet, capsule, powder, granules or pills, or by parenteral administration in the form of an injection, syrup, ointment or suppository. Although the dose varies according to the object of administration, administration route, symptoms and so forth, it is usually about 0.1 mg to 5 g per day, and preferably about 1 mg to 2 g per day, for a adult. This dose may be administered orally or parenterally either by dividing among 1–4 doses per day or at intervals of 1–7 days per dosing.

EXAMPLES

The following reference examples are typical examples of producing the carboxylic acid represented by the general formula (2). These examples are shown for the purpose of explaining the present invention but do not limit it. Furthermore, other carboxylic acids indicated with general formula (2) can also be synthesized by similar known methods or by performing some degree of modification.

Reference Example 1 Production Process of 4-(8-methoxythiochromanyl)methane carboxylic acid (wherein $R_6$, $R_7$=H, X=8-MeO, n=m=1 in formula (2))

(a) 2-(2-methoxyphenylthio)ethanecarboxylic acid (wherein X=2-MeO in formula (3))

1.5 ml of a solution of 1N sodium hydroxide in methanol are added to a solution of 20.2 g of 2-methoxybenzenethiol in 20 ml of methanol and 20 ml of diethyl ether followed by cooling to 0° C. 13.9 ml of methylacrylate was then dropwise added to this solution. After completion of dropping, the reaction mixture was warmed to room temperature and stirred overnight. After concentrating the reaction mixture by a rotary evaporator, 8.7 g of sodium hydroxide, 100 ml of water and 35 ml of methanol was added followed by stirring vigorously overnight. The reaction mixture was acidified with concentrated hydrochloric acid while cooling and the resulting solution was extracted with chloroform. The chloroform layer was dried with magnesium sulfate, the solvent was distilled off and the resulting crystal was recrystallized from chloroform-hexane to obtain 25.4 g of the target 2-(2-methoxyphenylthio) ethanecarboxylic acid (yield: 83%, m.p.: 91°–91.5° C.).

¹HNMR (CDCl₃, ppm) δ 9.70 (1H, brs), 6.82–7.40 (4H, m), 3.91 (3H, s), 3.13 (2H, t, J=6.3 Hz), 2.65 (2H, t, J=6.3 Hz) IR (KBr, cm⁻¹) 2930, 1719, 1576, 1479, 1433, 1265, 1245, 1199, 1073, 1023, 917,743 Elementary Analysis: As $C_{10}H_{12}O_3S$ Calculated values: C 56.58% H 5.70% observed values: C 56.64% H 5.73%

(b) 8-methoxythiochroman-4-one (wherein X=8-MeO in formula (4))

8.64 g of phosphorous pentachloride was added to a solution of 8.0 g of 2-(2-methoxyphenylthio)ethanecarboxylic acid in 24 ml of benzene under the atmosphere of argon while cooling to 0° C. After stirring the reaction mixture for 20 minutes at 100° C., 9.13 ml of stannous tetrachloride was dropwise added to the mixture while cooling to −10° C. Following completion of dropping, the reaction mixture was warmed to 0° C. and stirred for 30 minutes. Next, 24 g of ice followed by 14 ml of concentrated hydrochloric acid were added followed by refluxing for about 30 minutes. After cooling the reaction mixture to room temperature, the organic layer was separated and the aqueous layer was extracted three times with benzene. After combining the organic layers and washing twice with water, the combined organic layer was dried over magnesium sulfate, the solvent was distilled off and the resulting crystal was recrystallized from ethyl acetate-hexane to obtain 5.53 g of the target compound 8-methoxythiochroman-4-one (yield: 76%, m.p.: 110°–110.5° C.).

¹HNMR (CDCl₃, ppm) δ 7.77 (1H, dd, J=1.5 Hz, 7.7 Hz), 7.12 (2H, m) , 3.92 (3H, s), 3.22 (2H, m), 2.93 (2H, m) IR (KBr, cm⁻¹) 1676, 1589, 1566, 1464, 1423, 1334, 1263, 1201, 1046, 1011, 787 Elementary Analysis: As $C_{10}H_{10}O_2S$ Calculated values: C 61.83% H 5.19% Observed values: C 61.7 8% H 5.23%

(c) 4-(8-methoxythiochromanyl)methanecarboxylic acid (wherein $R_6$, $R_7$=H, X=8-MeO, n=m=1 in formula (2))

1.64 g of sodium hydroxide was suspended in 25 ml of toluene under an atmosphere of argon followed by dropwise adding in 8.74 ml of ethyl diethylphosphonoacetate at room temperature. After evolution of hydrogen gas had ceased, a solution of 5.3 g of 8-methoxythiochroman-4-one in 22 ml of toluene was added followed by stirring overnight at room temperature. 40 ml of water was added to stop the reaction followed by extracting four times with 50 ml of diethyl ether. After combining the organic layers and drying over magnesium sulfate, the solvent was distilled off and the residue was applied to column chromatography using 60 g of silica gel and a developing solution of 8% ethyl acetate and 92% hexane to remove contaminating highly polar substances. After distilling off the solvent of the elution, the resulting organic substance was dissolved in 40 ml of ethanol and 30 ml of ethyl acetate followed by the addition of 5 g of 10% palladium carbon while cooling with ice. After replacing the air in the reaction vessel with hydrogen using a hydrogen balloon, the reaction mixture was warmed to room temperature and stirred for 4 days. After filtering out the 10% palladium carbon, the solvent was distilled off and the resulting oily substance was suspended in aqueous sodium hydroxide followed by refluxing for 4 hours in atmosphere of argon. After cooling to room temperature, the reaction mixture was washed twice with diethyl ether followed by acidifying the aqueous solution layer with concentrated hydrochloric acid. This solution was extracted four times with 30 ml of chloroform and dried according to a conventional method. After distilling off the solvent, the resulting solid residue was recrystallized from a mixed solvent of tetrahydrofuran-hexane to obtain 4.27 g of the target compound 4-(8-methoxythiochromanyl) methane carboxylic acid (yield: 71%, m.p.: 122°–125° C.).

¹HNMR (CDCl₃, ppm) δ 7.91 (1H, brs), 6.63–7.10 (3H, m), 3.89 (3H, s), 3.47 (1H, m), 3.01 (2H, m), 2.68 (2H, m), 2.16 (2H, m) IR (KBr, cm⁻¹) 2930, 1702, 1568, 1468, 1425, 1253, 971, 777 Elementary Analysis: As $C_{12}H_{14}O_3S$ Calculated values: C 60.48% H 5.92% Observed values: C 60.44% H 5.93%

The following examples are shown for the purpose of explaining the present invention, but do not limit the present invention in any way.

Example 1

2-[4-(2,2-dimethylthiochromanyl)]-1-trimethylsiloxy ethane-1,1-diphosphonate tetramethylester (wherein $R_1$, $R_2$, $R_3$, $R_4$=Me, $R_5$=SiMe₃, $R_6$, $R_7$=Me, X=H, n=m=1 in formula (1))

2.77 g of 4-(2,2-dimethylthiochromanyl) methane carboxylic acid (wherein, $R_6$, $R_7$=Me, X=H, n=m=1 in formula (2)) was dissolved in 25 ml of tetrahydrofuran in an atmosphere of argon followed by the addition of 20 μl of dimethylsulfoxide. After dropwise adding 1.04 ml of oxalic chloride to this solution at room temperature, the reaction mixture was stirred for 2 hours. After concentrating the reaction mixture under a reduced pressure to remove the excess oxalic chloride, the resulting solid was again dissolved in 25 ml of tetrahydrofuran followed by the addition of 1.37 ml of trimethylphosphite and stirring for 2 hours at room temperature. Subsequently, 2.30 ml of dimethyltrimethyl-silylphosphite was added to the solution, followed by additionally stirring for 2.5 hours at room temperature. After adding 80 ml of chloroform and 50 ml of water to the reaction mixture and stirring well, the organic layer was separated and the aqueous layer was extracted four times with 30 ml of chloroform. The organic layers were combined and dried over magnesium chloride, the solvent was distilled off, and the resulting oily substance was purified with a silica gel column (1% methanol/chloroform) to obtain 4.78 g of the target compound (yield: 80%).

¹HNMR (CDCl₃, ppm) δ 7.48 (1H, m), 7.06 (3H, m), 3.80–3.93 (12H, m), 3.42 (1H, m), 2.86 (1H, q, J=15.1 Hz), 2.40 (1H, dd, J=5.9 Hz, 13.7 Hz), 2.24 (1H, m), 1.78 (1H, dd, J=11.7 Hz, 13.2 Hz), 1.39 (3H, s), 1.38 (3H, s), 0.21 (9H, s) IR (liquid film, cm⁻¹) 3002, 2960, 2856, 1734, 1591, 1560, 1458, 1367, 1253, 1183, 1151, 1133, 1118, 1040, 893, 849, 754 Elementary Analysis: As $C_{20}H_{36}O_7SiSP_2$ Calculated values: C 47.04% H 7.11% Observed values: C 47.31% H 7.16%

Example 2

Monosodium 2-[4-(2,2-dimethylthiochromanyl)]-1-hydroxyethane-1,1-diphosphonate (wherein $R_1$, $R_2$, $R_3$=H, $R_4$=Na, $R_5$=H, $R_6$, $R_7$=Me, X=H, n=m=1 in formula (1))

4.78 g of the 2-[4-(2,2-dimethylthiochromanyl)]-1-trimethylsiloxy-ethane-1,1-diphosphonate tetramethylester (wherein, $R_1$, $R_2$, $R_3$, $R_4$=Me, $R_5$=SiMe₃, $R_6$, $R_7$=Me, X=H, n=m=1 in formula (1)) obtained in Example 1 was dissolved in 27 ml of methylene chloride in an atmosphere of argon. Next, 10.3 ml of trimethylsilyl bromide was added at room temperature followed by stirring for 72 hours. After concentrating the reaction mixture under a reduced pressure, the resulting oily substance was heated twice with 50 ml of methanol. After again concentrating under a reduced pressure, the resulting amorphous solid was suspended in 120 ml of water and converted to the monosodium form by addition of 0.786 g of sodium hydrogencarbonate. The resulting aqueous solution was treated with active charcoal, membrane filtered and lyophilized to obtain 3.47 g of the target monosodium diphosphonate (yield: 92%, decomposition temperature: 225°–230° C.).

$^1$HNMR ($D_2O$, ppm) δ 7.64 (1H, d, J=7.3 Hz), 7.23–7.13 (2H, m), 3.60 (1H, m), 2.81 (1H, m), 2.56 (1H, dd, J=5.9 Hz, 13.7 Hz), 2.19 (1H, m), 1.76 (1H, dd, J=11.2 Hz, 13.7 Hz), 1.39 (3H, s), 1.36 (3H, s) MS (FAB-MS) m/z=405 (M+H) Elementary Analysis: As $C_{13}H_{19}O_7SP_2Na$ Calculated values: C 38.62% H 4.74% Observed values: C 38.57 % H 4.75%

Example 3

2-[4-(6-chlorothiochromanyl)]-1-trimethylsiloxyethane-1,1-diphosphonate tetramethylester (wherein $R_1$, $R_2$, $R_3$, $R_4$=Me, $R_5$=SiMe$_3$, $R_6$, $R_7$=H, X=6-Cl, n=m=1 in formula (1))

The target compound was obtained in a yield of 77% according to the same procedure as Example 1 using 4-(6-chlorothiochromanyl)methanecarboxylic acid (wherein, $R_6$, $R_7$=H, X=6-Cl, n=m=1 in formula (2)) as a starting material.

$^1$HNMR (CDCl$_3$, ppm) δ 7.21 (1H, d, J=1.8 Hz), 7.00 (2H, m), 3.75–3.92 (12H, m), 3.45 (1H, m), 3.17 (1H, dt, J=3.7 Hz, 12.2 Hz), 2.90 (1H, dt, J=4.9 Hz, 12.8 Hz), 2.35–2.50 (2H, m), 2.23 (1H, m), 1.89 (1H, m), 0.21 (9H, s) IR (liquid film, cm$^{-1}$) 2960, 2856, 1466, 1253, 1183, 1137, 1048, 847, 756 Elementary Analysis: As $C_{18}H_{31}O_7ClSiSP_2$ Calculated values: C 41.82% H 6.04% Observed values: C 41.82% H 6.07%

Example 4

Monosodium 2-[4-(6-chlorothiochromanyl)]-1-hydroxyethane-1,1-diphosphonate (wherein $R_1$, $R_2$, $R_3$=H, $R_4$=Na, $R_5$=H, $R_6$, $R_7$=H, X=6-Cl, n=m=1 in formula (1))

The target compound (decomposition temperature: 234°–239° C.) was obtained in a yield of 62% according to the same procedure as Example 2 using the 2-[4-(6-chlorothiochromanyl)]-1-trimethylsiloxyethane- 1,1-diphosphonate tetramethylester (wherein $R_1$, $R_2$, $R_3$, $R_4$=Me, $R_5$=SiMe$_3$, $R_6$, $R_7$=H, X=6-Cl, n=m=1 in formula (1)) obtained in Example 3.

$^1$HNMR ($D_2O$, ppm) δ7.44 (1H, d, J=2.0 Hz), 7.13 (2H, m), 3.62 (1H, m), 3.27 (1H, dr, J=3.4 Hz, 12.2 Hz), 2.98 (1H, dt, J=4.4 Hz, 12.7 Hz), 2.54 (1H, ddd, J=4.4 Hz, 8.3 Hz, 14.2 Hz), 2.15–2.40 (2H, m), 1.88 (1H, m) MS (FAB-MS) m/z=410 (M-H) Elementary Analysis: As $C_{11}H_{14}O_7ClSP_2Na$ Calculated values: C 32.17% H 3.44% Measured values: C 32.15% H 3.41%

Example 5

2-(4-thiochromanyl)-1-trimethylsiloxyethane-1,1-diphosphonate tetramethylester (wherein $R_1$, $R_2$, $R_3$, $R_4$=Me, $R_5$=SiMe$_3$, $R_6$, $R_7$=H; X=H, n=m=1 in formula (1))

The target compound was obtained in 97% yield according to the same procedure as Example 1 using 4-thiochromanylmethanecarboxylic acid (wherein $R_6$, $R_7$=H, X=H, n=m=1 in formula (2)).

$^1$HNMR (CDCl$_3$, ppm) δ 7.17 (1H, m), 6.96–7.08 (3H, m), 3.77–3.92 (12H, m), 3.48 (1H, m), 3.22 (1H, dr, J=3.9 Hz, 12.2 Hz), 2.88 (1H, td, J=4.4 Hz, 12.2 Hz), 2.55 (1H, m), 2.43 (1H, m), 2.22 (1H, m), 1.92 (1H, tt, J=3.9 Hz, 12.7 Hz), 0.21 (9H, s) IR (liquid film, cm$^{-1}$) 3060, 2960, 2856, 1589, 1568, 1473, 1441, 1270, 1183, 1156, 1135, 1060, 859, 758 Elementary Analysis: As $C_{18}H_{32}O_7SiSP_2$ Calculated values: C 44.80% H 6.69% Measured values: C 44.83% H 6.73%

Example 6

Monosodium 2-(4-thiochromanyl)-1-hydroxyethane-1,1-diphosphonate (wherein $R_1$, $R_2$, $R_3$=H, $R_4$=Na, $R_5$=H, $R_6$, $R_7$=H, X=H, n=m=1 in formula (1))

The target compound (decomposition temperature: 218°–223° C.) was obtained in yield of 83% according to the same procedure as Example 2 using the 2-(4-thiochromanyl)-1-trimethylsiloxyethane-1,1-diphosphonate tetramethylester (wherein $R_1$, $R_2$, $R_3$, $R_4$=Me, $R_5$=SiMe$_3$, $R_6$, $R_7$=H, X=H, n=m=1 in formula (1)) obtained in Example 5.

$^1$HNMR ($D_2O$, ppm) δ 7.39 (1H, m), 7.08–7.16 (3H, m), 3.64 (1H, m), 3.29 (1H, dt, J=3.4 Hz, 12.7 Hz), 2.97 (1H, td, J=4.4 Hz, 12.7 Hz), 2.58 (1H, m), 2.37 (1H, m), 2.21 (1H, m), 1.91 (1H, m) MS (FAB-MS) m/z=377 (M+H) Elementary Analysis: As $C_{11}H_{15}O_7SP_2Na$ Calculated values: C 35.11% H 4.02% Observed values: C 35.12% H 4.07%

Example 7

2-[4-(8-chlorothiochromanyl)]-1-trimethylsiloxyethane-1,1-diphosphonate tetramethylester (wherein $R_1$, $R_2$, $R_3$, $R_4$=Me, $R_5$=SiMe$_3$, $R_6$, $R_7$=H, X=8-Cl, n=m=1 in formula (1))

The target compound was obtained in a 78% according to the same procedure as Example 1 using 4-(8-chlorothiochromanyl)methanecarboxylic acid (wherein $R_6$, $R_7$=H, X=8-Cl, n=m=1 in formula (2)).

$^1$HNMR (CDCl$_3$, ppm) δ 7.17 (1H, dd, J=1.5 Hz, 7.8 Hz), 7.11 (1H, d, J=6.8 Hz), 6.93 (1H, t, J=7.8 Hz), 3.77–3.92 (12H, m), 3.53 (1H, m), 3.24 (1H, dt, J=3.4 Hz, 12.7 Hz), 2.94 (1H, td, J=4.4 Hz, 12.7 Hz), 2.59 (1H, m), 2.42 (1H, m), 2.16 (1H, m), 1.85 (1H, m), 0.22 (9H, s) IR (liquid film, cm$^{-1}$) 2960, 2856, 1450, 1419, 1251, 1183, 1137, 1036, 849, 779, 754 Elementary Analysis: As $C_{18}H_{31}O_7ClSiSP_2$ Calculated values: C 41.82% H 6.04% Measured values: C 41.85% H 6.09%

Example 8

Monosodium 2-[4-(8-chlorothiochromanyl)]-1-hydroxyethane-1,1-diphosphonate (wherein $R_1$, $R_2$, $R_3$=H, $R_4$=Na, $R_5$=H, $R_6$, $R_7$=H, X=8-Cl, n=m=1 in formula (1))

The target compound (decomposition temperature: 198°–205° C.) was obtained in a yield of 98% according to the same procedure as Example 2 using the 2-[4-(8-chlorothiochromanyl)]-1-trimethylsiloxyethane- 1,1-diphosphonate (wherein $R_1$, $R_2$, $R_3$, $R_4$=Me, $R_5$=SiMe$_3$, $R_6$, $R_7$=H, X=8-Cl, n=m=1 in formula (1)) obtained in Example 7.

$^1$HNMR ($D_2O$, ppm) δ 7.35 (1H, d, J=7.8 Hz), 7.28 (1H, dd, J=1.5 Hz, 8.3 Hz), 7.08 (1H, t, J=8.3 Hz), 3.71 (1H, m), 3.32 (1H, dr, J=3.4 Hz, 12.7 Hz), 3.05 (1H, td, J=3.9 Hz, 12.2 Hz), 2.62 (1H, m), 2.33 (1H, m), 2.17 (1H, m), 1.84 (1H, m) MS (FAB-MS) m/z=411 (M+H) Elementary Analysis: As $C_{11}H_{14}O_7ClSP_2Na$ Calculated values: C 32.17% H 3. Observed values: C 32.13% H 3.48%

Example 9

2-[4-(8-ethylthiochromanyl)]-1-trimethylsiloxyethane-1,1-diphosphonate tetramethylester (wherein $R_1$, $R_2$, $R_3$, $R_4$=Me, $R_5$=SiMe$_3$, $R_6$, $R_7$=H, X=8-Et, n=m=1 in formula (1))

The target compound was obtained in an 83% yield according to same procedure as Example 1 using 4-(8-ethylthiochromanyl)methanecarboxylic acid (wherein $R_6$, $R_7$=H, X=8-Et, n=m=1 in formula (2)).

$^1$HNMR (CDCl$_3$, ppm) δ 6.94–7.05 (3H, m), 3.72–3.95 (12H, m), 3.51 (1H, m), 3.20 (1H, dt, J=4.0 Hz, J=12.5 Hz), 2.91 (1H, td, J=4.0 Hz, J=12.5 Hz), 2.63 (2H, q, J=7.3 Hz), 2.55 (1H, m), 2.42 (1H, m), 2.23 (1H, m), 1.88 (1H, m), 1.23 (3H, t, J=7.3 Hz), 0.21 (9H, s) IR (liquid film, cm$^{-1}$) 2962, 2858, 1462, 1431, 1253, 1183, 1158, 1137, 1065, 857, 760 Elementary Analysis: As $C_{20}H_{36}O_7SiSP_2$ Calculated values: C 47.04% H 7.11% Observed values: C 47.01% H 7.16%

Example 10

Disodium 2-[4-(8-ethylthiochromanyl)]-1-hydroxyethane-1,1-diphosphonate (wherein $R_1$, $R_3$=H, $R_2$, $R_4$=Na, $R_5$=H, $R_6$, $R_7$=H, X=8-Et, n=m=1 in formula (1))

The target compound (decomposition temperature: 228°–234° C.) was obtained in an 88% yield according to the same procedure as Example 2 of using the 2-[4-(8-ethylthiochromanyl)]-1-trimethylsiloxyethane- 1,1-diphosphonate tetramethylester (wherein $R_1$, $R_2$, $R_3$, $R_4$=Me, $R_5$=SiMe$_3$, $R_6$, $R_7$=H, X=8-Et, n=m=1 in formula (1)) obtained in Example 9, and forming the disodium salt using two equivalents of sodium hydrogencarbonate.

$^1$HNMR (D$_2$O, ppm) δ 7.28 (1H, m), 7.10 (3H, m), 3.70 (1H, m), 3.31 (1H, dt, J=3.4 Hz, J=12.2 Hz), 3.01 (1H, m), 2.63 (1H+2H, m), 2.34 (1H, m), 2.17 (1H, m), 1.85 (1H, m), 1.18 (3H, t, J=7.3 Hz) MS (FAB-MS) m/z=427 (M+H) Elementary Analysis: As $C_{13}H_{18}O_7SP_2Na_2$ Calculated values: C 36.63% H 4.26% Observed values: C 36.60% H 4.31%

Example 11

2-[4-(8-methoxythiochromanyl)]-1-trimethylsiloxyethane-1,1-diphosphonate tetramethylester (wherein $R_1$, $R_2$, $R_3$, $R_4$=Me, $R_5$=SiMe$_3$, $R_6$, $R_7$=H, X=8-MeO n=m=1 in formula (1))

The target compound was obtained in a 79% yield according to the same procedure as Example 1 using 4-(8-methoxythiochromanyl)methanecarboxylic acid (wherein $R_6$, $R_7$=H, X=8-MeO, n=m=1 in formula (2)).

$^1$HNMR (CDCl$_3$, ppm) δ 6.97 (1H, t, j=7.7 Hz), 6.84 (1H, d, J=7.3 Hz), 6.65 (1H, d, J=8.1 Hz), 3.76–3.92 (12H+3H, m), 3.50 (1H, m), 3.18 (1H, dt, J=3.3 Hz, 12.5 Hz), 2.88 (1H, td, J=4.0 Hz, 12.5 Hz), 2.58 (1H, m), 2.43 (1H, m), 2.21 (1H, m), 1.87 (1H, m), 0.22 (9H, s) IR (liquid film, cm$^{-1}$) 2956, 2856, 1572, 1435, 1245, 1015, 820 Elementary Analysis: As $C_{19}H_{34}O_8SiSP_2$ Calculated values: C 44.52% H 6.69% Observed values: C 44.99% H 6.73%

Example 12

Disodium 2-[4-(8-methoxythiochromanyl)-1-hydroxethane-1,1-diphosphonate (wherein wherein $R_1$, $R_3$=H, $R_2$, $R_4$=Na, $R_5$=H, $R_6$, $R_7$=H, X=8-MeO, n=m=1 in formula (1))

The target compound (decomposition temperature: 228°–265°–270° C.) was obtained in a 91% yield according to the same procedure as Example 2 with the exception of using the 2-[4-(8-methoxythiochromanyl)]-1-trimethylsiloxyethane-1,1-diphosphonate tetramethylester (wherein $R_1$, $R_2$, $R_3$, $R_4$=Me, $R_5$=SiMe$_3$, $R_6$, $R_7$=H, X=8-MeO, n=m=1 in formula (1)) obtained in Example 11, and forming the disodium salt using two equivalents of sodium hydrogencarbonate.

$^1$HNMR (D$_2$O, ppm) δ 7.09–7.15 (2H, m), 6.86 (1H, dd, J=2.0 Hz, 7.3 Hz), 3.86 (3H, s), 3.68 (1H, m), 3.25 (1H, dr, J=3.4 Hz, 12.7 Hz), 2.97 (1H, td, J=3.9 Hz, 12.7 Hz), 2.62 (1H, m), 2.29 (1H, m), 2.17 (1H, m), 1.84 (1H, m) MS (FAB-MS) m/z=429 (M+H) Elementary Analysis: As $C_{12}H_{16}O_8SP_2Na_2$ Calculated values: C 33.65% H 3.77% Observed values: C 33.61% H 3.81%

Example 13

2-[4-(8-methylthiothiochromanyl)]-1-trimethylsiloxyethane-1,1-diphosphonate tetramethylester (wherein $R_1$, $R_2$, $R_3$, $R_4$=Me, $R_5$=SiMe$_3$, $R_6$, $R_7$=H, X=8-MeS, n=m=1 in formula (1))

The target compound was obtained in a 97% yield according to the same procedure as Example 1 using 4-(8-methylthiothiochromanyl)methanecarboxylic acid (wherein $R_6$, $R_7$=H, X=8-MeS, n=m=1 in formula (2)).

$^1$HNMR (CDCl$_3$, ppm) δ 6.97–7.08 (3H, m), 3.76–3.92 (12H, m), 3.51 (1H, m), 3.25 (1H, dt, J=3.9 Hz, 12.7 Hz), 2.96 (1H, td, J=4.4 Hz, 12.2 Hz), 2.57 (1H, m), 2.47 (3H, s), 2.44 (1H, m), 2.19 (1H, m), 1.87 (1H, m), 0.21 (9H, s) IR ( liquid film, cm$^{-1}$) 2958, 2856, 1446, 1408, 1257, 1183, 1158, 1135, 1048, 849, 756 Elementary Analysis: As $C_{19}H_{34}O_7SiS_2P_2$ Calculated values: C 43.17% t{ 6.48% Observed values: C 43.12% H 6.51%

Example 14

Disodium 2-[4-(8-methylthiothiochromanyl)]-1-hydroxyethane-1,1-diphosphonate (wherein $R_1$, $R_3$=H, $R_2$, $R_4$=Na, $R_5$=H, $R_6$, $R_7$=H, X=8-MeS, n=m=1 in formula (1))

The target compound (decomposition temperature: 275°–280° C.) was obtained in a 98% yield according to the same procedure as Example 2 with the exception of using the 2-[4-(8-methylthiothiochromanyl)]- 1-trimethylsiloxyethane-1,1-diphosphonate tetramethylester (wherein $R_1$, $R_2$, $R_3$, $R_4$=Me, $R_5$=SiMe$_3$, $R_6$, $R_7$=H, X=8-MeS, n=m=1 in formula (1)) obtained in Example 13, and forming the disodium salt using two equivalents of sodium hydrogencarbonate.

$^1$HNMR (D$_2$O, ppm) δ 7.31 (1H, d, J=7.3 Hz), 7.14–7.20 (2H, m), 3.71 (1H, m), 3.35 (1H, dr, J=3.4 Hz, 12.2 Hz), 3.05 (1H, td, J=3.9 Hz, 12.7 Hz), 2.63 (1H, m), 2.49 (3H, s), 2.31 (1H, m), 2.16 (1H, m), 1.83 (1H, m) MS (FAB-MS) m/z= 445 (M+H) Elementary Analysis: As $C_{12}H_{16}O_7S_2P_2Na_2$ Calculated values: C 32.44% H 3.63% Observed values: C 32.39% H 3.67%

Example 15

Adjuvant Arthritis Test

Polyarthritis resembling human rheumatoid arthritis occurs when tubercule bacillus adjuvant is injected into rats. Using this adjuvant arthritis model, the anti-inflammatory and antirheumatic actions of the compounds of the present invention were investigated according to the procedure described below.

0.5 mg of dried non-viable tubercule bacillus (*Mycobacterium butyricum*) were suspended in 0.1 ml of liquid paraffin and injected into the skin of the left hind limb of 7 week old Lewis female rats. The compounds obtained in the working examples were dissolved in sterile distilled water and administered subcutaneously daily for 2 weeks from the 8th day to the 21st day after the day of adjuvant injection at a rate of 3 or 20 mg per kg of body weight. During that time, the volumes of the left and right hind limbs were measured and the swelling rate was calculated according to the equation below.

Swelling rate=[limb volume on 14th or 21st day (ml)—limb volume on 7th day (ml)/[limb volume on 7th day]×100
Moreover, the swelling inhibition rates were determined using the following equation, and those results are shown in Table 1.

Swelling inhibition rate=[Mean swelling rate of control group—mean swelling rate of compound dose group]/[mean swelling rate of control group]×100

The rats were sacrificed on the 22nd day, and soft X-ray radiographs were taken of both the left and right hind limbs. The degree of bone destruction at 5 locations of the left and right hind limbs was evaluated by assigning scores from five levels, respectively, based on the soft X-ray radiographs. The total score was then taken to be the bone destruction score. Moreover, bone destruction inhibition rates were calculated using the equation below, the results of which are shown in Table 1.

Bone destruction inhibition rate=[mean bone destruction score of control group—mean bone destruction score of compound administration group]/[mean bone destruction score of control group]×100

The results were analyzed using the student's t-test and Dunnett's multiple comparison method. Those results that were significantly different at a level of significance of $p<0.001$ from the control group administered with only sterile distilled water were indicated with three asterisks (*), those significantly different at a level of significance of $p<0.01$ were indicated with two asterisks (), and those significantly different at a level of significance of $p<0.05$ were indicated with one asterisk (*).

As is clear from Table 1, limb swelling and bone destruction caused by primary and secondary inflammation of adjuvant arthritis were inhibited by the compounds according to the present invention.

TABLE 1

| Compound | (mg/kg) | Swelling inhibition rate with respect to control group (%) | | | | Bone destruction inhibition rate with respect to control group (%) |
|---|---|---|---|---|---|---|
| | | 14th day | | 21st day | | |
| | | Left | Right | Left | Right | |
| Compound of Example 2 | 20 | 59.6 ** | 8.0 | 75.3*** | 16.5 * | 80.4 ** |
| Compound of Example 4 | 3 | 55.5 ** | 32.4 | 93.0*** | 37.7 ** | 52.7 ** |
| Compound of Example 6 | 3 | 26.1 | 27.2 | 62.0*** | 35.9 ** | 38.5 ** |
| Compound of Example 8 | 3 | 52.6*** | 0.1 | 84.1*** | 37.5*** | 52.3 ** |
| Compound of Example 10 | 3 | 38.1 ** | 19.5 | 62.5*** | 33.9 ** | 23.9 ** |
| Compound of Example 12 | 3 | 35.4 ** | 0.2 | 60.1*** | 24.2 * | 26.2 ** |
| Compound of Example 14 | 3 | 53.9*** | 2.9 | 80.0*** | 31.0 ** | 46.9 ** |

INDUSTRIAL APPLICABILITY

Since the compounds of the present invention have anti-inflammatory action, antipyretic and analgesic action, or action which improves bone abnormalities caused by rheumatism, arthritis, osteoporosis and so forth, they are useful as an anti-inflammatory, antipyretic, analgesic, anti-rheumatism drug, antiarthritic or anti-osteoporosis drug. Moreover, since the hydroxydiphosphonate synthesis method of the present invention enables the reaction to be carried out more easily and under mild conditions, thereby allowing it to be applied to synthesis of a wider range of hydroxydiphosphonate derivatives, it is useful as a synthetic method for the compound of the hydroxydiphosphonate structure.

We claim:

1. A methane diphosphonic acid derivative represented by the general formula (1):

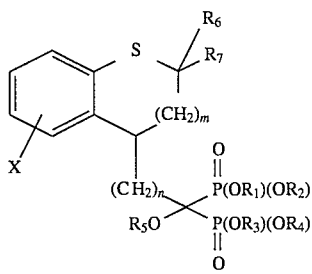

(1)

wherein $R_1$, $R_2$, $R_3$ and $R_4$ are independently a pharmacologically acceptable cation, a hydrogen atom or a straight chain or branched alkyl group having 1–4 carbon atoms, $R_5$ is a hydrogen atom or a trialkylsilyl group having 1–6 carbon atoms, m is an integer of 0 to 3, n is an integer of 1 to 3, $R_6$ and R7 are independently a hydrogen atom or an alkyl group having 1–4 carbon atoms, and X represents a hydrogen atom, a halogen atom, a straight chain or branched alkyl group having 1–8 carbon atoms, a straight chain or branched alkoxy group having 1–8 carbon atoms, or an alkylthio group having a straight chain or branched alkyl portion of 1–8 carbon atoms.

2. A process for producing a methane diphosphonic acid derivative defined in claim 1, comprising the steps of:

sequentially reacting carboxylic acid of the following general formula (2):

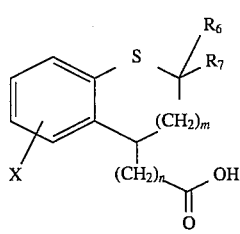

(2)

wherein $R_6$, $R_7$, X, m and n are as defined in claim 1,
with an acid chloride forming agent, trialkylphosphite and dialkyltrialkylsilylphosphite.

3. The process for producing a methane diphosphonic acid derivative according to claim 2, wherein m is 1.

4. A process for producing a methane diphosphonic acid derivative defined in claim 1, comprising the steps of:

sequentially reacting carboxylic acid of the following general formula (2):

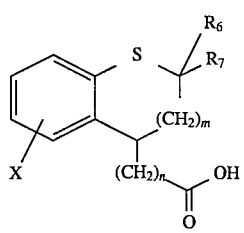

(2)

$R_6$, $R_7$, X, m and n are as defined in claim 1, with an acid chloride forming agent at room temperature, with trialkylphosphite for 0.5–5.0 hours and with dialkyltrialkylsilylphosphite.

5. The methane diphosphonic acid derivative according to claim 1, produced by sequentially reacting carboxylic acid of the following general formula (2):

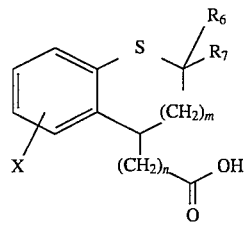

(2)

wherein $R_6$, $R_7$, X, m and n are as defined in claim 1,
with an acid chloride forming agent, trialkylphosphite and dialkyltrialkylsilylphosphite.

6. The methane diphosphonic acid derivative according to claim 5, wherein m is 1.

7. A method of treating inflammation comprising a pharmaceutically effective application of a methane diphosphonic acid derivative according to claim 1.

8. A method of treating rheumatism comprising a pharmaceutically effective application of a methane diphosphonic acid derivative according to claim 1.

9. A method of treating bone metabolic disease comprising a pharmaceutically effective application of a methane diphosphonic acid derivative according to claim 1.

10. The methane diphosphonic acid derivative according to claim 1, produced by sequentially reacting carboxylic acid of the following general formula (2):

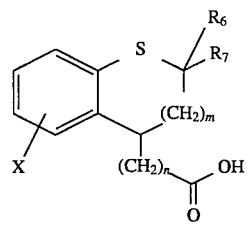

(2)

wherein $R_6$, $R_7$, X, m and n are as defined in claim 1,
with an acid chloride forming agent, with trialkylphosphite for 0.5–5.0 hours and with dialkyltrialkylsilylphosphite.

11. The methane diphosphonic acid derivative according to claim 1, wherein m is 1.

12. A method of treating inflammation comprising a pharmaceutically effective application of a methane diphosphonic acid derivative according to claim 11.

13. A method of treating rheumatism comprising a pharmaceutically effective application of a methane diphosphonic acid derivative according to claim 11.

14. A method of treating bone metabolic disease comprising a pharmaceutically effective application of a methane diphosphonic acid derivative according to claim 11.

15. A pharmaceutical composition comprising a methane diphosphonic acid derivative according to claim 1 and a pharmaceutically acceptable carrier.

16. A pharmaceutical composition comprising a methane diphosphonic acid derivative according to claim 11 and a pharmaceutically acceptable carrier.

* * * * *

UNITED STATES PATENT AND TRADEMARK OFFICE
CERTIFICATE OF CORRECTION

PATENT NO. : 5,565,440
DATED : October 15, 1996
INVENTOR(S) : Keijiro Takanishi et al It is certified that error appears in the above-indentified patent and that said Letters Patent is hereby corrected as shown below:

Column 3, line 29, please change "R5" to --$R_5$--.

Column 9, line 46, please change "$R_2$" to --$R_2$--.

Column 11, line 1, please change "H 3." to --H 3.44%--.

Column 12, line 43, please change "t{" to --H--.

Signed and Sealed this

Twenty-ninth Day of July, 1997

Attest:

BRUCE LEHMAN

Attesting Officer     Commissioner of Patents and Trademarks